(12) United States Patent
Ramalingam et al.

(10) Patent No.: US 10,398,726 B1
(45) Date of Patent: Sep. 3, 2019

(54) TEMPLATE-FREE METHOD OF PREPARING ZEOLITES FROM BIOMASS

(71) Applicant: KING SAUD UNIVERSITY, Riyadh (SA)

(72) Inventors: Jothi Ramalingam, Chennai (IN); Jesu Doss, Riyadh (SA); Judith Vijaya, Chennai (IN); Hamad Al-Lohedan, Chennai (IN)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/118,373

(22) Filed: Aug. 30, 2018

(51) Int. Cl.
| | | |
|---|---|---|
| *A61K 33/06* | (2006.01) | |
| *A61P 35/00* | (2006.01) | |
| *A61K 33/24* | (2019.01) | |
| *C01B 39/38* | (2006.01) | |
| *A61K 33/34* | (2006.01) | |

(52) U.S. Cl.
CPC .............. *A61K 33/06* (2013.01); *A61K 33/24* (2013.01); *A61K 33/34* (2013.01); *A61P 35/00* (2018.01); *C01B 39/38* (2013.01); *C01P 2004/64* (2013.01)

(58) Field of Classification Search
CPC ......... A61K 33/06; A61K 33/24; A61P 35/00; C01B 39/38; C01P 2004/64
See application file for complete search history.

(56) References Cited

U.S. PATENT DOCUMENTS

| | | | |
|---|---|---|---|
| 5,023,392 A | 6/1991 | Han | |
| 5,023,393 A | 6/1991 | Han | |
| 6,368,571 B1 | 4/2002 | Vempati | |
| 2004/0170694 A1* | 9/2004 | Colic | A61K 9/143 424/490 |

FOREIGN PATENT DOCUMENTS

| | | | |
|---|---|---|---|
| CN | 104909385 | | 9/2015 |
| IN | 201741007518 A | * | 9/2018 |
| MX | 2008003003 | | 9/2009 |

OTHER PUBLICATIONS

Dey et al. "Organic templkate free synthesis of ZSM-5 zeolite particles using rice husk as as silica source" in Ceramic International 39 (2013) 2153-2157.*

Yue et al. ("Template-Free Synthesis and Catalytic Applications of Microporous and Hierarchical ZSM-5 Zeolites from Natural Aluminosilicate Minerals" in Indian Engineering Chemical Research) 2017, pp. 10069-10077.*

B. Jha and D.N. Singh, Fly Ash Zeolites, Advanced Structured Materials 78, Chapter 2, Basics of Zeolite, pp. 1-31, 2016.*

Hu et al, Adsorptioon of copper valerate oin zeolite H-ZSM-5, 1997.*

Kodatos, K., et al., "Synthesis of Highly Siliceous ZSM-5 Zeolite Using Silica from Rice Husk Ash," Microporous and Mesoporous Materials (115)1-2: pp. 189-196 (2008).

Salama, T.M., et al., "Novel Synthesis of Nay Zeolite from Rice Husk Silica: Modification with Zno and Zns for Antibacterial Application," Chem. Sci. J., (7)118 (2016).

Karlsson, H.L., et al., "Copper Oxide Nanoparticles are Highly Toxic: A Comparison between Metal Oxide Nanoparticles and Carbon Nanotubes," Chem. Res. Toxicol. (21) pp. 1726-1732 (2008).

Kaviyarasu, K., et al., "In Vitro Cytotoxicity Effect and Antibacterial Performance of Human Lung Epithelial Cells A549 Activity of Zinc Oxide doped TiO2 Nanocrystals: Investigation of Bio-medical Application by Chemical Method," Materials Science & Engineering (2016).

Akhtar, M. J., et al., "Zinc Oxide Nanoparticles Selectively Induce Apoptosis in Human Cancer Cells Through Reactive Oxygen Species," International J. of Nanomedicine, (7) pp. 845-857 (2012).

Samiei, M., et al., "Zeolite-Silver-Zinc Nanoparticles: Biocompatibility and their Effect on the Compressive Stength of Mineral Trioxide Aggregate," J. Clin. Exp. Dent. (9)3: pp. 356-360 (2017).

* cited by examiner

Primary Examiner — Blessing M Fubara
(74) Attorney, Agent, or Firm — Richard C. Litman

(57) ABSTRACT

A template-free method of preparing zeolites from biomass can include using rice husk ash waste material as a precursor material. The zeolites can include ZSM-5 zeolites, such as, hierarchical pure zeolites and metal-loaded (Cu, Ni) ZSM-5 zeolites. This method allows for production of zeolites in a low cost and environmentally friendly manner. These ZSM-5 zeolites may be used for numerous applications, including killing cancer cells. The cancer cells may be human lung cancer cells.

4 Claims, 6 Drawing Sheets

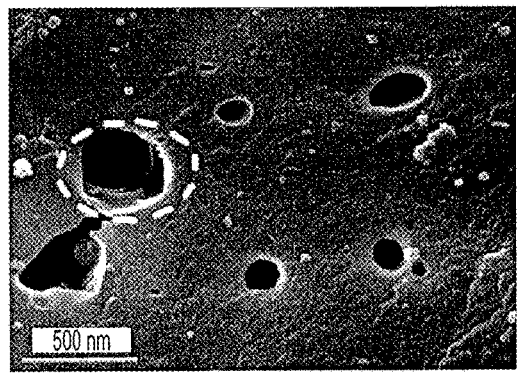
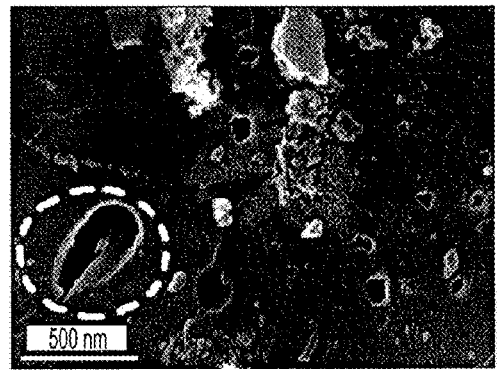
FIG. 3A  FIG. 3B
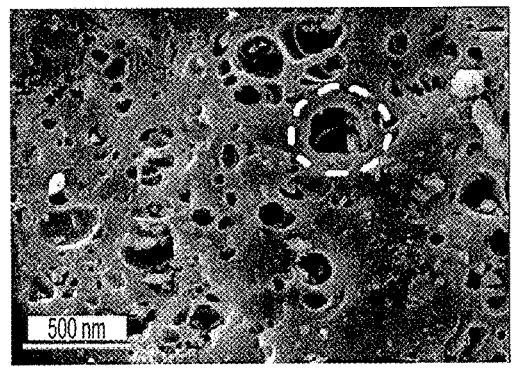
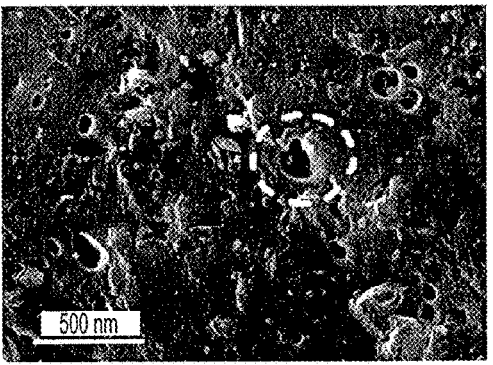
FIG. 3C  FIG. 3D

TEMPLATE-FREE METHOD OF PREPARING ZEOLITES FROM BIOMASS

BACKGROUND

1. Field

The disclosure of the present patent application relates to zeolites, and particularly to template free zeolites prepared from biomass.

2. Description of the Related Art

Lung cancer is one of the most common causes of cancer-related deaths; in recent years more than one million deaths per year are reported worldwide. The survival rate of patients with lung cancer is very poor, with only 15% of patients surviving for 5 years after diagnosis. The most commonly attributed cause of lung cancer is smoking, which has been linked to 9 out of 10 patients suffering from lung cancer. Further risk factors include exposure to asbestos material, chromium, nickel, arsenic, radon, vinyl chloride and ionizing radiation. Human lung cancer is categorized in two histopathological subtypes: ~80% non-small cell lung cancer (NSCLC), further classified as adenocarcinoma, squamous cell, and large cell carcinomas and 20% small-cell lung cancer (SCLC), which are termed pulmonary tumors.

The most common treatment for lung cancer is chemotherapy. However, this treatment often fails due to complications arising from premature extra thoracic spreading and continual disease decline. New chemotherapy agents and radiotherapy treatments have enhanced the survival rate and improved quality of life for patients. Still, severe side effects have been reported for antitumor chemotherapeutics. Recent strategies for developing new anti-cancer agents have included investigations of metal nanoparticles.

Zeolites are microporous, aluminosilicate materials that can temporarily store a wide variety of cations. Zeolite catalysts are used in many petrochemical industries for various uses, including, conversions, isomerizations, cracking, and alkylation reactions, because of their superior properties such as hydrothermal durability, elevated surface area, strong acidity, strength, and shape selectivity. ZSM-5 or Zeolite Socony Mobil-5 (framework type MFI from ZSM-5 (five)), is an aluminosilicate zeolite belonging to the pentasil family of zeolites. Prior methods for preparing ZSM-5 zeolites generally include use of organic templates. Such methods typically include use of tetraalkylammonium cations (TAAs) or amines, which cannot be recycled, and when they are thermally removed, they release $CO_2$ and hazardous nitrous oxides.

Thus, a template-free method of synthesizing ZSM-5 zeolites solving the aforementioned problems are desired.

SUMMARY

A template-free method of preparing zeolites from biomass can include using rice husk ash waste material as a precursor material. The zeolites can include ZSM-5 zeolites, such as, hierarchical pure zeolites and metal-loaded (Cu, Ni) ZSM-5 zeolites. This method allows for production of zeolites in a low cost and environmentally friendly manner. These ZSM-5 zeolites may be used for numerous applications, including killing cancer cells.

These and other features of the present disclosure will become readily apparent upon further review of the following specification and drawings.

BRIEF DESCRIPTION OF THE DRAWINGS

FIG. 3A is a high-resolution scanning electron micrograph of a hierarchical pure zeolite.

FIG. 3B is a high-resolution scanning electron micrograph of a hierarchical pure zeolite.

FIG. 3C is a high-resolution scanning electron micrograph of a 1% Cu-ZSM-5 zeolite.

FIG. 3D is a high-resolution scanning electron micrograph of a 3% Cu-ZSM-5 zeolite.

DETAILED DESCRIPTION OF THE PREFERRED EMBODIMENTS

Figure 1:
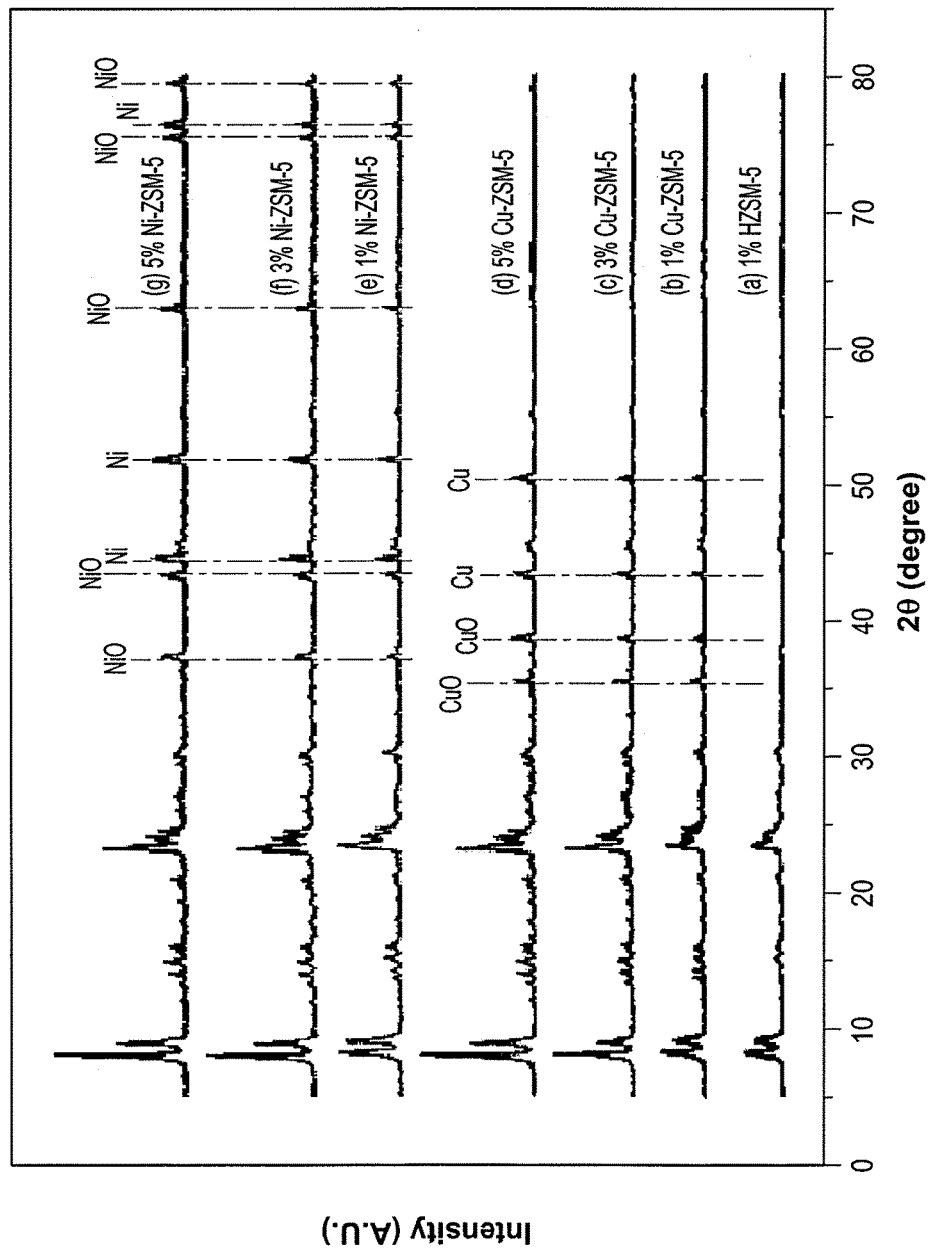
FIG. 1 is a plot of X-ray diffraction patterns of hierarchical pure and M-ZSM-5 (1%, 3%, and 5%) zeolites.

A template-free method for preparing zeolites from biomass includes using rice husk ash ("RHA") waste material as a precursor material. The zeolites can include Zeolite Socony Mobil-5 (hereinafter, "ZSM-5 zeolites"). ZSM-5 zeolites are aluminosilicate zeolites belonging to the pentasil family of zeolites. The ZSM-5 zeolites can include hierarchical pure ZSM-5 zeolites and metal-loaded ZSM-5 zeolites (hereinafter, "M-ZSM-5 zeolites"). The M-ZSM-5 zeolites can include copper-loaded ZSM-5 zeolites (hereinafter, "Cu-ZSM-5 zeolites") and/or nickel-loaded ZSM-5 zeolites (hereinafter, Ni-ZSM-S zeolites). Other water-based precursor materials can also be used. The method allows for production of ZSM-5 zeolites without the use of organic templates. As such, the ZSM-5 zeolites can be produced in a low cost and environmentally friendly manner. The ZSM-5 zeolites may be used for numerous applications, including killing cancer cells.

The method can provide highly crystalline, hierarchical pure and M-ZSM-5 zeolites using a hydrothermal route that does not require using organic templates. The method is green or environmentally friendly, easy to perform, economical, recyclable, and requires less synthesis time. The resulting hierarchical pure and M-ZSM-S zeolites may be highly crystalline, without impurities. The zeolites can be porous, including several small-sized nanoparticles and porous surfaces. The zeolites can have an octahedron-like, non-spherical morphology. The zeolite particles can be about 3 nm in size.

The ZSM-5 zeolites may be useful in treating cancer. In an embodiment, the cancer may be lung cancer. The zeolites may kill lung cancer cells by one or more routes, including, triggering oxidative stress, mitochondrial dysfunction, and programmed cell death (apoptosis). The lung cancer cells may be human lung cancer cells. The concentration of zeolites used to treat cancer may be between about 23.2 µg/ml and about 1,000 µg/ml. In an embodiment, the concentration of hierarchical pure zeolites used may be about 23.2 µg/ml, 51.3 µg/ml, 89.5 µg/ml, 175 µg/ml, 250 µg/ml, 500 µg/ml, or 1,000 µg/ml. In an embodiment, the concentration of Ni-ZSM-5 zeolites used may be about 29.7 µg/ml, 47.3 µg/ml, 58.1 µg/ml, 68.7 µg/ml, 125 µg/ml, 500 µg/ml, or 1,000 µg/ml. In an embodiment, the concentration of Cu-ZSM-5 zeolites used may be about 27.5 µg/ml, 41.6 µg/ml, 68.3 µg/ml, 137 µg/ml, 250 µg/ml, 500 µg/ml, or 1,000 µg/ml.

The zeolites may be manufactured by washing rice husk pellets, drying them in an electric oven, and then burning the rice husk pellets to ash. In an embodiment the burning may be performed in a programmable muffle furnace at about 550° C. for about 5 hours, to produce RHA. The RHA may then be suspended in water and mixed with a solution of aluminum and sodium hydroxide to produce aluminosilicate gel. In an embodiment, the aluminum may be aluminum foil and the mixing may include continuous stirring for about 10 hours at room temperature. The aluminosilicate gel may then be heated in crystallization range, cooled, filtered, and washed until the pH approaches neutral. The resulting reaction mixture may then be dried and calcined to provide sodium ZSM-5 ("Na-ZSM-5").

Na-ZSM-5 may be transformed to hierarchical pure hydrogen ZSM-5 zeolites or H-ZSM-5 zeolites by continuous ion-exchange in excess aqueous $NH_4NO_3$. This reaction mixture may be filtered, washed, dried, and calcined to produce hierarchical pure H-ZSM-5 zeolites.

Hierarchical pure H-ZSM-5 zeolites may be transformed into M-ZSM-5 zeolites by the incipient wet impregnation method. The H-ZSM-5 zeolites may be impregnated with a solution of 1%, 3%, or 5% $Cu(NO_3)_2 6H_2O$ or $Ni(NO_3)_2 6H_2O$, dried and calcined to produce 1%, 3%, and 5% M-ZSM-5 zeolites, respectively.

The present teachings are illustrated by the following examples.

Example 1

Template Free Synthesis of Hierarchical Pure and Metal-Loaded ZSM-5 Zeolites

Rice husk pellets, a silica-rich waste material, were acquired from rice millers in Trichirappalli district, Tamilnadu, India and thoroughly washed with double distilled water 2-3 times in order to remove the outer surface impurities. The washed rice husk pellets were dried in electric oven at about 80° C. for about 2 hours to remove external moisture and burnt to ash, using a programmable muffle furnace at about 550° C. for about 5 hours, with a heating and cooling rate of 2° C. $min^{-1}$ to produce crystalline RHA.

A first solution was formed by suspending about 9.45 g RHA in about 71 ml of deionized water. A second solution was formed by mixing about 0.04 g of aluminum metal foil and about 2.4 g of NaOH in about 10 ml of deionized water. The first and second solutions were then mixed under continuous stirring for about 10 hours at room temperature, resulting in a dispersed solution of aluminosilicate gel with a molar ratio of $100SiO_2:0.5Al_2O_3:20Na_2O:3000H_2O$. The dispersed solution was placed in a Teflon-lined stainless steel autoclave and continuously heated in crystallization range at about 100° C. under autogenous pressure for about 3 days. After the hydrothermal reaction, the reaction mixture was cooled, filtered, and thoroughly washed several times with distilled water until pH reached almost neutral. The reaction mixture was dried overnight at about 60° C. and calcined in a muffle furnace at about 300° C. for about 3 hours using heating and cooling rates of about 1° C. to 2° C. per minute.

The sodium form of hierarchical ZSM-5 zeolite powder was obtained and this Na-ZSM-5 catalyst was transformed into the hydrogen form by continuous ion-exchange using excess 1M aqueous $NH_4NO_3$. The total amount of $NH_4NO_3$ used was around 10 ml/g of zeolite catalyst. Subsequently, the reaction mixture was filtered, washed, and dried at about 60° C. for about 4 hours and calcined at about 300° C. for about 3 hours to remove the remaining humidity, ammonia and ammonium nitrate from the H-ZSM-5.

M-ZSM-5 zeolites were primed by the incipient wet impregnation method. An appropriate quantity of the H-ZSM-5 was impregnated solely with an aqueous solution of $Cu(NO_3)_2 6H_2O$ or $Ni(NO_3)_2 6H_2O$ (1%, 3%, and 5% respectively) at room temperature for about 5 hours, dried in air oven at about 60° C. overnight, and calcined at about 300° C. for 2 h. The resulting catalysts were labeled as 1% Cu-ZSM-5, 3% Cu-ZSM-5, 5% Cu-ZSM-5 and 1% Ni-ZSM-5, 3% Ni-ZSM-5, 5% Ni-ZSM-5 respectively.

Example 2

XRD and FTIR Analysis

FIG. 1 shows the powder X-ray diffraction (XRD) patterns of hierarchical pure and M-ZSM-5 (1%, 3% and 5%) zeolite samples and it reveals the typical diffraction peaks of MFI crystalline structure. All tested materials revealed characteristic X-ray diffraction pattern peaks at $2\theta=7.9°$, 9.04°, 13.59°, 14.19°, 15.14°, 15.91°, 23.38°, 24.16°, 25.63° and 30.18° that are related with (101), (111), (102), (112), (131), (022), (051), (313), (323) and (062) planes, the typical structure of ZSM-5 (JCPDS no. 89-1421). No impurity peaks were observed, indicating the high purity of the samples. In FIG. 1 (b-d), two characteristic peaks were detected for CuO at $2\theta=35.4°$, 38.6° (JCPDS no. 89-2531), and the resultant Miller indices (002) and (111). For Cu, one peak was observed at $2\theta=43.34°$ (JCPDS no. 04-0836), corresponding to plane (111). From FIG. 1 (e-g), three characteristic peaks were observed for nickel at $2\theta=44.5°$, 51.8°, and 76.4°, corresponding to the Miller indices (111), (200), and (220), respectively. The peak positions indicate that the synthesized zeolite materials are purely face-centered cubic (fcc) nickel (JCPDS no. 04-0850). The intensity lines increase with an increase in the metal loading (%), when compared with the hierarchical ZSM-5 zeolites. The XRD pattern evidently shows the transformation of CuO to Cu and NiO to Ni, confirming that all CuO was reduced to Cu and all NiO was reduced to Ni.

Figure 2:
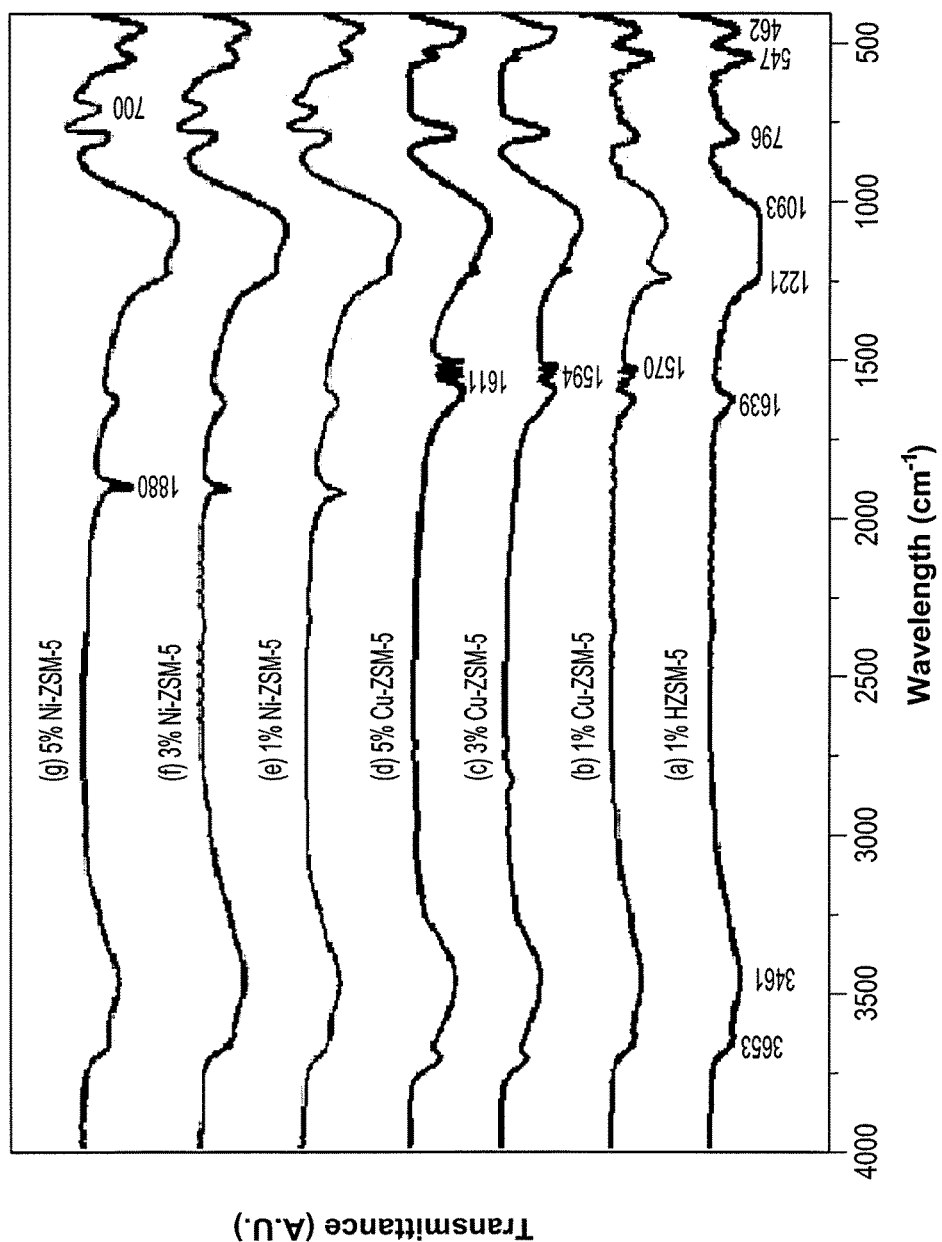
FIG. 2 is a plot of FTIR spectra of hierarchical pure and M-ZSM-5 (1%, 3%, and 5%) zeolites.
Figure 3E:
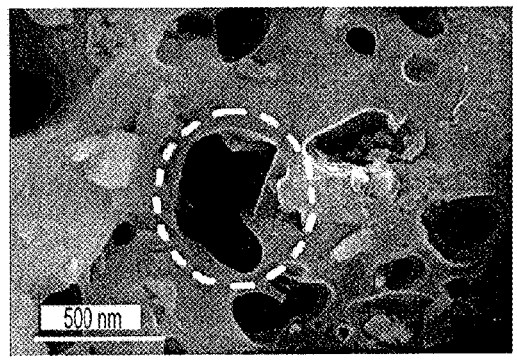
FIG. 3E is a high-resolution scanning electron micrograph of a 5% Cu-ZSM-5 zeolite.
Figure 3F:
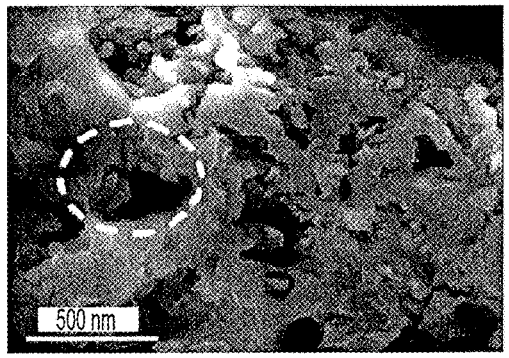
FIG. 3F is a high-resolution scanning electron micrograph of a 1% Ni-ZSM-5 zeolite.
Figure 3G:
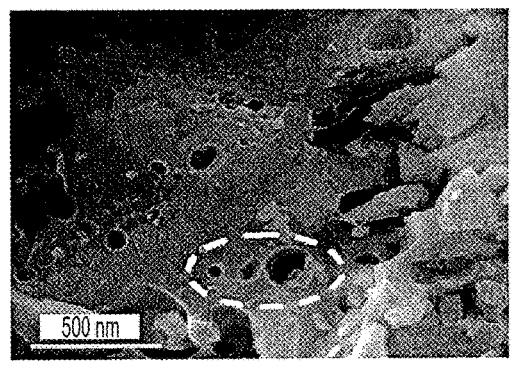
FIG. 3G is a high-resolution scanning electron micrograph of a 3% Ni-ZSM-5 zeolite.
Figure 3H:
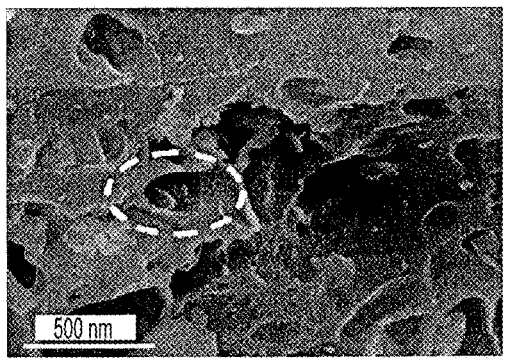
FIG. 3H is a high-resolution scanning electron micrograph of a 5% Ni-ZSM-5 zeolite.

FTIR spectral studies were recorded in the range of 4000-400 $cm^{-1}$ and are illustrated in FIG. 2. The characteristic absorption band at 462 $cm^{-1}$ is due to the T-O bending vibration mode of the $(Si, Al)O_4$ internal tetrahedral sites. The band at 796 $cm^{-1}$, 1093 $cm^{-1}$ and 1221 $cm^{-1}$ is due to the external symmetric stretching, internal asymmetric stretching and external asymmetric stretching respectively and correspond to siliceous materials. The bending vibration mode of 1639 $cm^{-1}$ is attributed to the water molecules in the zeolite framework. The broad peaks at 3653 $cm^{-1}$ and 3461 $cm^{-1}$ indicate the isolated silanol groups (Si—O—H)

and Al—OH framework (Brønsted acid sites) respectively. The vibration band at 547 cm$^{-1}$ is assigned to the presence of D$_5$R (double 5 rings) composed of tetrahedral SiO$_4$ and AlO$_4$ units in the ZSM-5 structure. Thus, the addition of Cu and Ni metal ions to the zeolites has not destroyed the ZSM-5 zeolite framework. In FIG. 2 (b-d), the peaks at 1611 cm$^{-1}$, 1594 cm$^{-1}$ and 1570 cm$^{-1}$ show the anti-symmetric and symmetric stretches of nitrate species on Cu$^{2+}$ ion and from FIG. 2 (e-g), the peaks at 700 cm$^{-1}$ and 1880 cm$^{-1}$ can be imputed to the nitrate ion groups present in Ni$^{2+}$ of MFI frame ZSM-5 zeolites. Thus, both the XRD and FTIR studies confirmed that the M-ZSM-5 samples have MFI type ZSM-5 structure.

Example 3

HR-SEM Analysis

The HR-SEM measurements were carried out on as-synthesized hierarchical pure and M-ZSM-5 zeolite samples prepared from biomass waste material and the contained morphologies are displayed in FIGS. 3A-3H. The HR-SEM images exposed that hierarchical pure (FIGS. 3A-3B, different magnification scales) and different wt % (1%, 3%, and 5%) concentrations of Cu-ZSM-5 (FIGS. 3C-3E) and Ni-ZSM-5 (FIGS. 3F-3H) result in porous surface morphology and irregular shape, which is common in template-free systems. Additionally, several larger particles (about 50 nm to 100 nm) and lots of small particles (about 15 to 25 nm) appear on the surface, due to the agglomeration. The surface of the samples was slightly rougher; it may be accredited to the nanosized hierarchical ZSM-5 zeolite particles. HR-SEM images of the HZSM-5, Cu-ZSM-5 and Ni-ZSM-5 morphologies have shown that the external shape of ZSM-5 nanoparticles is approximately maintained. The SEM images demonstrate that the petite apertures have porous nanostructures. From the synthesis processes, silicates (SiO$_4$)$^{4-}$ and aluminate ions (Al(OH)$_4^-$) are associated with Na$^+$ metal ions to form hierarchical ZSM-5 zeolites and this alkali metal ion acted as a supporting mediator for the formation of ZSM-5. Crystalline silica was suspended gradually during the synthesis in alkali intermediates and used to enrich silica for the superior development of the ZSM-5. Also, the inner growth of the silica, alumina and metal ion particles, explains the channel-type arrangement of the crystalline porous-like nanostructures.

Example 4

HR-TEM Analysis

The high-resolution transmission electron microscopy (HR-TEM) was also utilized to visualize the nanostructures of the synthesized hierarchical pure and M-ZSM-5 zeolites. The monodispersed hierarchical ZSM-5 zeolite structures were found to possess nearly non-spherical octahedron-like nanocrystals with individually high agglomeration in the particle size range of about 1-10 nm. Nanoparticles of various sizes in the range of about 1 to about 10 nm were observed, with the most common particle size being about 3 nm. HR-TEM showed that tiny individual ZSM-5 nanoparticles have a highly single crystalline nature, as confirmed by selective area electron diffraction ("SAED") and the lattice fringes. SAED identified visible diffraction spots with the crystalline planes zone axis as (101), (111), (102), (112), (131), (022), (051), (313), (323) and (062), which are in good agreement with the MFI-type structure and also with the XRD pattern. These crystalline features are observed in the very small size of the individual zeolite nanoparticles. In the major cases, the nanocrystal ranges are below approximately 10 nm, an average particle size of approximately 3 nm.

Example 5

N$_2$ Adsorption/Desorption Isotherm Studies

Figure 4:
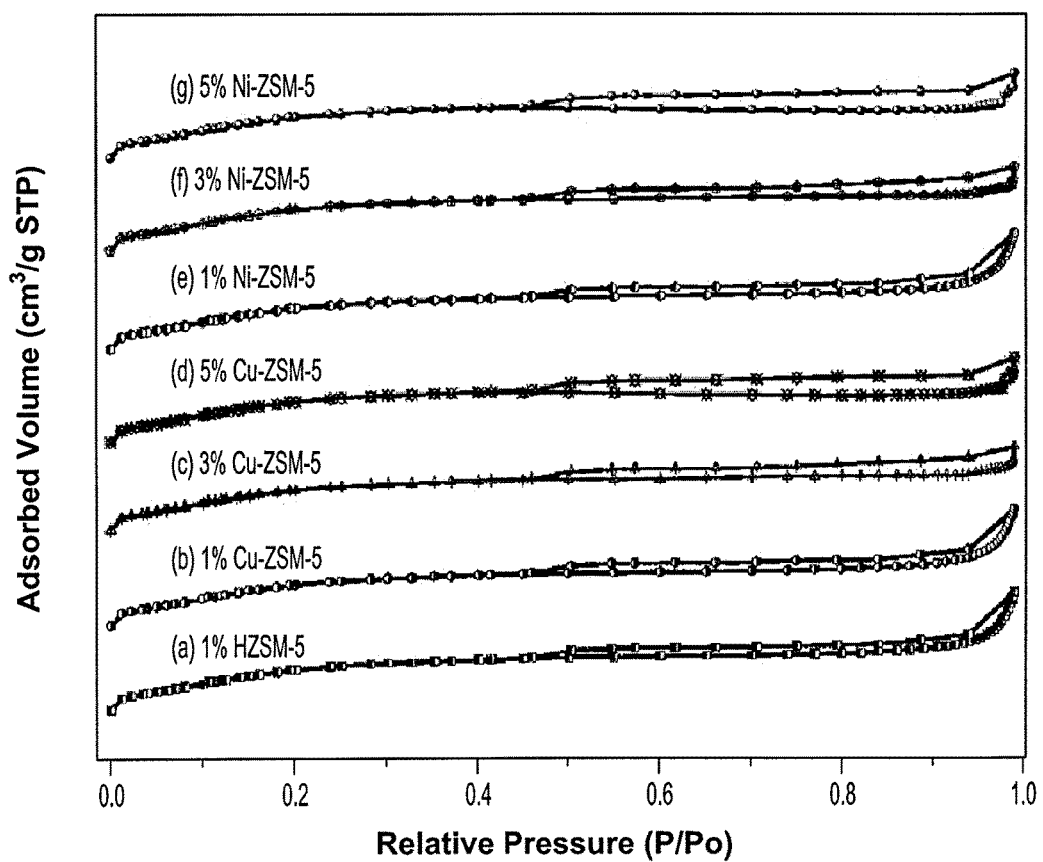
FIG. 4 is a graph of $N_2$ absorption/desorption isotherms of hierarchical pure and 1%, 3%, and 5% M-ZSM-5 zeolites.

The N$_2$ adsorption/desorption isotherms studies infer the structural and textural properties of the as-synthesized catalysts and are clarified in FIG. 4. All of the zeolites showed typically type IV isotherms with a vertical uptake under P/P$_0$=0.02 and a hysteresis loop from P/P$_0$=0.45 to P/P$_0$=1. This is due to the consistency of both micropores and mesopores. The observed fixing at a low relative pressure region (P/P$_0$<0.02) implies the micropores. 5% M-ZSM-5 zeolites' hysteresis loops are slightly broader than the other M-ZSM-5 (1% and 3%) and H-ZSM-5 zeolites, which confirm the formation of extra mesoporosity (FIG. 4). In hierarchical ZSM-5 zeolites, mesoporosity is due to inter-crystalline voids created by accumulated nanoparticles. The extra mesoporosity present in 5% M-ZSM-5 samples was not affected by the microporosity structure, and it may allow swift diffusion of reactant molecules and enhanced catalytic and biomedical activity. Textural parameters, including the BET surface area, micropore surface area, mesopore surface area, total pore volume, micropore volume, and mesopore volume were obtained using the BET equation and the t-plot method (Table 1). From the data presented in Table 1 it appears that increasing the amount of copper and nickel metal species manipulates small differences in surface area and micropore volume. Increasing metal loading in a zeolite framework decreases the microporosity. High concentrations of metal species may lead to de-alumination, partial blockage of channels, aggregation of zeolite nanoparticles and a decrease in surface area and micropore volumes. Thus, the N$_2$ adsorption/desorption isotherm results confirmed the formation of the hierarchical pure and M-modified (Cu, Ni) ZSM-5 zeolite structures. These typical hierarchical structures play an essential role in various catalytic and biomedical applications.

TABLE 1

Textural Parameters of HZSM-5 and M-ZSM-5 Zeolites

| | S$_{BET}$ (m$^2$/g) | S$_{MICRO}$ (m$^2$/g) | S$_{MESO}$ (m$^2$/g) | V$_{TOTAL}$ (cm$^2$/g) | V$_{MICRO}$ (cm$^2$/g) | V$_{MESO}$ (cm$^2$/g) |
|---|---|---|---|---|---|---|
| HZSM-5 | 145.83 | 99.86 | 45.97 | 0.0725 | 0.0348 | 0.0377 |
| 1% Cu-ZSM-5 | 141.65 | 86.56 | 55.0 | 0.0710 | 0.0325 | 0.0385 |
| 3% Cu-ZSM-5 | 137.98 | 78.82 | 59.16 | 0.0686 | 0.0296 | 0.0390 |
| 5% Cu-ZSM-5 | 135.88 | 72.75 | 63.13 | 0.0665 | 0.0254 | 0.04111 |
| 1% Ni-ZSM-5 | 142.93 | 85.64 | 57.29 | 0.0715 | 0.0326 | 0.0389 |
| 3% Ni-ZSM-5 | 139.38 | 77.98 | 61.40 | 0.0692 | 0.0299 | 0.0393 |
| 5% Ni-ZSM-5 | 136.12 | 70.50 | 65.62 | 0.0674 | 0.0260 | 0.0414 |

Example 6

In Vitro Anticancer Activity

Immortalized human epithelial A549 NSCLC cells line (LTR Center, Chennai) were used to test cell viability. The A549 cells were full-grown in the sub-cultured Dulbecco's modified Eagle's medium (DMEM), supplemented with 2.5 g/L glucose, 2 mM L-glutamine, 5% fetal bovine serum (FBS), 1% penicillin/streptomycin, and 10 mM HEPES. All cell lines were incubated in a humidified incubator at 37° C. supplied with 5% $CO_2$.

The MTT assay was used to estimate the viability of A549 cells treated with varying concentrations of M-ZSM-5 zeolites. The cells were diffused and incubated at 37° C. under 5% $CO_2$ humidified atmosphere. The cells were incubated with M-ZSM-5 zeolites of varying concentrations for about 15 hours. Then the samples were detached from the media and washed with phosphate-buffered saline (pH 7.4) or DMEM without serum. About 10 µl/well of 0.5% 3-(4,5-dimethyl-2-thiazolyl)-2,5-diphenyl-tetrazolium bromide ("MTT") was added to each well and incubated for about 2 hours. After the incubation period, about 1 ml of DMSO was added to each well and the absorbance value was measured at 570 nm using a UV-spectrophotometer. DMSO was used as a reference. The percent of cell viability was calculated as the mean absorbance value for each hierarchical pure and M-ZSM-5 zeolite sample concentration divided by the mean value of control cells. All trials were carried out at least three times. All data are represented as the mean value of three parallel experiments. The data were expressed as means SD. (standard deviation). Intergroup variations were analyzed by one-way Analysis of Variance (ANOVA), followed by Turkey's test and it was accepted at a level of $p<0.05$.

Figure 5B:
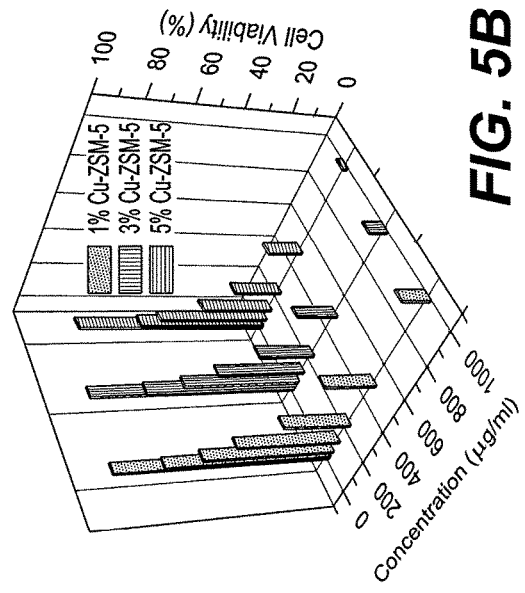
FIG. 5B is a graph of MTT assay measurements of A549 cell viability when treated with multiple concentrations of 1%, 3%, and 5% Cu-ZSM-5.
Figure 5C:
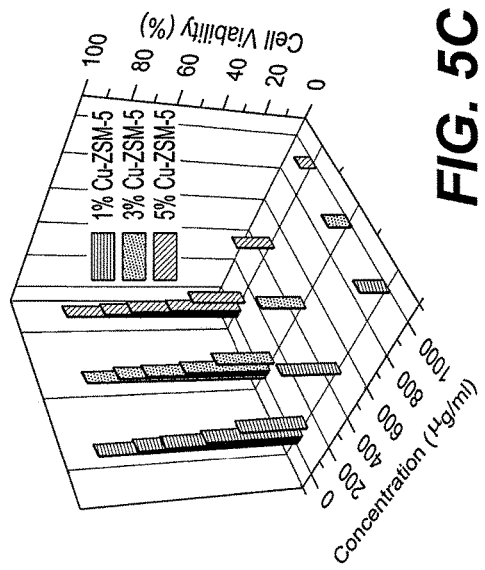
FIG. 5C is a graph of MTT assay measurements of A549 cell viability when treated with multiple concentrations of 1%, 3%, and 5% Ni-ZSM-5.
Figure 5A:
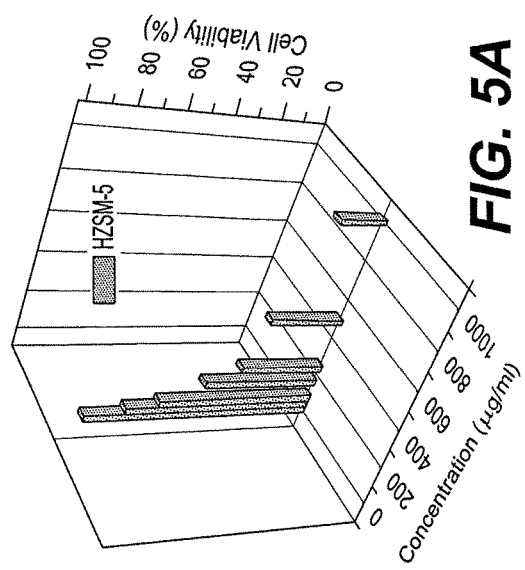
FIG. 5A is a graph of MTT assay measurements of A549 cell viability when treated with multiple concentrations of hierarchical pure zeolites.

The MTT assay established significant cytotoxic effects of the M-ZSM-5 zeolites on human lung cancer A549 cells lines at different concentration (23.2-1000 µg/ml). Table 2 shows the different percentage of cell viability treated at different concentrations of the hierarchical pure and M-ZSM-5 (1%, 3%, and 5%) zeolites. 5% Cu-ZSM-5 zeolites show superior cytotoxic activity than other hierarchical ZSM-5 zeolites, because the cell viability counts consecutively decreases in the pure and metal loaded ZSM-5 zeolites. These values mainly depend on the dosage level. The graphs in FIGS. 5A-5C illustrate the % cell viability measured after treatment with different concentrations of hierarchical pure and 1%, 3%, and 5% M-ZSM-5 zeolites. At sample concentration of 1000 µg/mL, lower cell viability is observed: about 20.1% (H-ZSM-5), about 07.5% (5% Ni-ZSM-5), about 02.5% (5% Cu-ZSM-5). The cell viability increased gradually as the concentration of zeolites used decreased to: about 95.0% (23.2 µg/mL H-ZSM-5), about 83.8% (29.7 µg/mL 5% Ni-ZSM-5), about 82.0% (27.5 µg/mL 5% Cu-ZSM-5).

Cell morphology of A549 human lung cancer cell lines treated with various concentrations of hierarchical pure and 5% Cu/Ni-ZSM-5 zeolites were altered. This confirms that the hierarchical 5% Cu-ZSM-5 zeolites show superior cytotoxic effects towards the A549 human lung cancer cell lines than other source materials. The cells treated with various amounts of hierarchical ZSM-5 zeolites are altered morphologically due to the swelling and breaking of cells. Accordingly, the release of 5% Cu-ZSM-5 nanoparticles into A549 cells can perform as an exogenous carrier and finally result in oxidative stress. It can be concluded that the greater cytotoxic efficiency of hierarchical 5% Cu-ZSM-5 zeolites lead to a large number of reactive oxygen species during mitochondrial dysfunction in both direct and indirect manner and thus lead to cell death.

Hierarchical pure and M-modified (Cu, Ni) ZSM-5 zeolites (1%, 3%, and 5%) achieves cytotoxic effects in a dose-dependent manner, which was calculated by the MTT assay. A significant role in the cytotoxic mechanisms is correlated with metal ZSM-5 zeolite nanoparticles that is exposed to oxidative stress. The highly crystalline hierarchical pure and metal modified ZSM-5 nanoparticles induced oxidative stress leads to DNA damage and apoptosis. The cytotoxicity results demonstrate that the hierarchical pure and M-modified (Cu, Ni) ZSM-5 zeolites synthesized from biomass-derived rice husk ash can effectively inhibit human lung cancer (A549) cell lines and is reported for the first time.

It is to be understood that the template-free method of preparing zeolites from biomass is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A template free method of fabricating zeolites, comprising:
   drying rice husk pellets to provide dried rice husk
   burning the dried rice husk to provide a rice husk ash, wherein the step of obtaining rice husk ash comprises:
   drying rice husk pellets in an electric oven at about 80° C. for about 2 hours; and
   burning the dried rice husk pellets in a muffle furnace at about 550° C. for about 5 hours to provide the rice husk ash;
   suspending the rice husk ash in water to produce a first solution;
   mixing aluminum, water, and NaOH to produce a second solution;

TABLE 2

| MTT Assay | | | | | | | | |
|---|---|---|---|---|---|---|---|---|
| H-ZSM-5 | | Ni-ZSM-5 | | | | Cu-ZSM-5 | | |
| Sample | | Sample | Cell viability | | | Sample | Cell viability | | |
| (µg/ml) | Cell viability (%) | (µg/ml) | 1% | 3% | 5% | (µg/ml) | 1% | 3% | 5% |
| 1000 | 20.1 | 1000 | 14.3 | 11.0 | 7.5 | 1000 | 12.7 | 08.4 | 02.5 |
| 500 | 31.5 | 500 | 27.9 | 21.7 | 18.5 | 500 | 22.5 | 18.1 | 15.7 |
| 250 | 35.8 | 125 | 32.5 | 29.6 | 27.2 | 250 | 29.2 | 25.4 | 21.3 |
| 175 | 49.6 | 68.7 | 46.1 | 42.5 | 36.0 | 137 | 44.7 | 38.5 | 32.1 |
| 89.5 | 66.5 | 58.1 | 64.6 | 60.2 | 54.3 | 68.3 | 56.0 | 50.9 | 48.4 |
| 51.3 | 79.1 | 47.3 | 75.6 | 72.1 | 66.7 | 41.6 | 70.6 | 65.8 | 56.2 |
| 23.2 | 95.0 | 29.7 | 91.8 | 85.7 | 83.8 | 27.5 | 90.2 | 88.3 | 82.0 | mixing the first solution and the second solution to provide an aluminosilicate gel:

heating the aluminosilicate gel at about 100° C. for about 3 days to provide a heated reaction mixture;

cooling the heated reaction mixture to provide a cooled reaction mixture;

filtering the cooled reaction mixture to provide a powder;

calcining the powder to produce a sodium-loaded zeolite catalyst, wherein the powder is calcined in a muffle furnace at 300° C. for 3 hours;

transforming the sodium-loaded zeolite catalyst to a pure hydrogen zeolite catalyst by continuous ion-exchange using excess aqueous NH4N03, wherein the zeolite catalyst is Zeolite Socony Mobil-5 (ZSM-5) zeolite catalyst; and impregnating the ZSM-5 zeolite catalyst with an aqueous solution of 5% $Cu(NO_3)_2.(H_2O)_6$ to provide a Cu-loaded ZSM-5 zeolite catalyst.

2. The zeolite of claim 1, wherein the zeolite has a particle size of about 3 nm.

3. The zeolite of claim 1, wherein the zeolite has a generally octahedral morphology.

4. A template free method of fabricating zeolites, comprising:

drying rice husk pellets to provide dried rice husk burning the dried rice husk to provide a rice husk ash, wherein the step of obtaining rice husk ash comprises:

drying rice husk pellets in an electric oven at about 80° C. for about 2 hours; and burning the dried rice husk pellets in a muffle furnace at about 550° C. for about 5 hours to provide the rice husk ash;

suspending the rice husk ash in water to produce a first solution;

mixing aluminum, water, and NaOH to produce a second solution;

mixing the first solution and the second solution to provide an aluminosilicate gel:

heating the aluminosilicate gel at about 100° C. for about 3 days to provide a heated reaction mixture;

cooling the heated reaction mixture to provide a cooled reaction mixture;

filtering the cooled reaction mixture to provide a powder;

calcining the powder to produce a sodium-loaded zeolite catalyst, wherein the powder is calcined in a muffle furnace at 300° C. for 3 hours;

transforming the sodium-loaded zeolite catalyst to a pure hydrogen zeolite catalyst by continuous ion-exchange using excess aqueous NH4N03, wherein the zeolite catalyst is Zeolite Socony Mobil-5 (ZSM-5) zeolite catalyst; and impregnating the ZSM-5 zeolite catalyst with an aqueous solution of 5% $Ni(NO_3)_2.(H_2O)_6$ to provide a Ni-loaded ZSM-5 zeolite catalyst.

* * * * *